Figure 2:
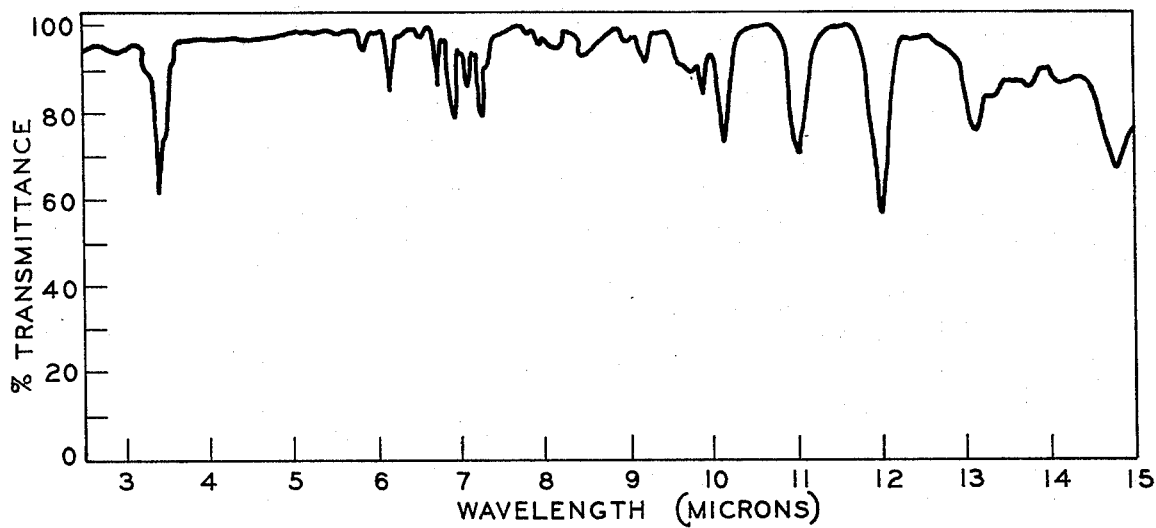

United States Patent [19]

Allen

[11] 3,998,887

[45] Dec. 21, 1976

[54] p-STYRYLDIETHYLPHOSPHINE

[75] Inventor: James D. Allen, Bartlesville, Okla.

[73] Assignee: Phillips Petroleum Company, Bartlesville, Okla.

[22] Filed: June 7, 1974

[21] Appl. No.: 477,178

Related U.S. Application Data

[62] Division of Ser. No. 832,729, June 12, 1969, Pat. No. 3,847,997.

[52] U.S. Cl. .................. 260/606.5 P; 260/604 HF; 260/632 HF; 526/275; 526/12; 526/47; 526/48
[51] Int. Cl.$^2$ .......................................... C07F 9/50
[58] Field of Search ............................ 260/606.5 P

[56] References Cited
UNITED STATES PATENTS

| | | | |
|---|---|---|---|
| 3,010,998 | 11/1961 | Garner | 260/606.5 P |
| 3,065,210 | 11/1962 | Abramo et al. | 260/606.5 P X |
| 3,152,104 | 10/1964 | Rabinowitz et al. | 260/606.5 P X |
| 3,824,221 | 7/1974 | Ragg | 260/80 PS |

Primary Examiner—Helen M. S. Sneed

[57] ABSTRACT

Hydroformylation reactions are carried out in the presence of a catalyst comprising a solid polymer of a trivalent phosphorus-containing compound having associated therewith a metal of the group cobalt, rhodium, ruthenium, platinum and palladium. The polymer, which can be formed in part of a polyvinylaromatic compound, can be used to remove catalyst residues from hydroformylation reaction effluent streams. p-styryldiethylphosphine and polymers thereof are disclosed.

1 Claim, 2 Drawing Figures p-STYRYLDIETHYLPHOSPHINE

This application is a division of copending application Ser. No. 832,729, filed June 12, 1969, now U.S. Pat. No. 3,847,997.

It is well known that various olefins can be reacted with carbon monoxide and hydrogen so as to be converted into corresponding aldehydes and/or alcohols. These reactions are often referred to as oxo or hydroformylation reactions. In the past, dicobalt octacarbonyl has commonly been used as a catalyst for carrying out reactions of this type. A typical known reaction is one in which the catalyst comprises dissolved cobalt in a concentration of approximately 2,000 parts per million in the reaction zone. Unfortunately, substantial amounts of the catalyst are dissolved in the reaction products and must eventually be recovered. The recovery of catalyst from the reaction products is a relatively expensive operation and greatly increases the cost of the process. It is also known that reactions of this type can be carried out by use of catalyst systems which comprise a complex of a metal, such as cobalt, and a phosphorus-containing ligand, see U.S. Pat. Nos. 3,168,553, 3,239,566, 3,239,571, 3,290,379 and 3,369,050, for example. However, catalyst removal is still a problem in these systems.

It has been found that an improved catalyst system for use in oxo reactions can be formed by combining conventional oxo catalysts, such as dicobalt octacarbonyl, with a solid support formed of a trivalent phosphorus-containing polymer. By use of a catalyst system of this type, it is possible to maintain the concentration of metal in the reaction zone at a relatively low level. This greatly simplifies the removal of catalyst residues from the reaction products. In addition, a system can be provided for recovering catalyst residues from the reaction products in the oxo process by passing the reactor effluent through a bed of the phosphorus-containing polymer. The polymer serves to remove catalyst residues from reaction products, and in so doing forms a material which can subsequently be used as the catalyst system in an oxo process. In accordance with one aspect of this invention, p-styryldiethylphosphine is provided as a new compound. In accordance with another aspect of this invention, polymers of p-styryldiethylphosphine are provided. These polymers can be employed as the polymer in the above-described processes. These polymers can have metals deposited thereon to form catalysts.

Figure 1:
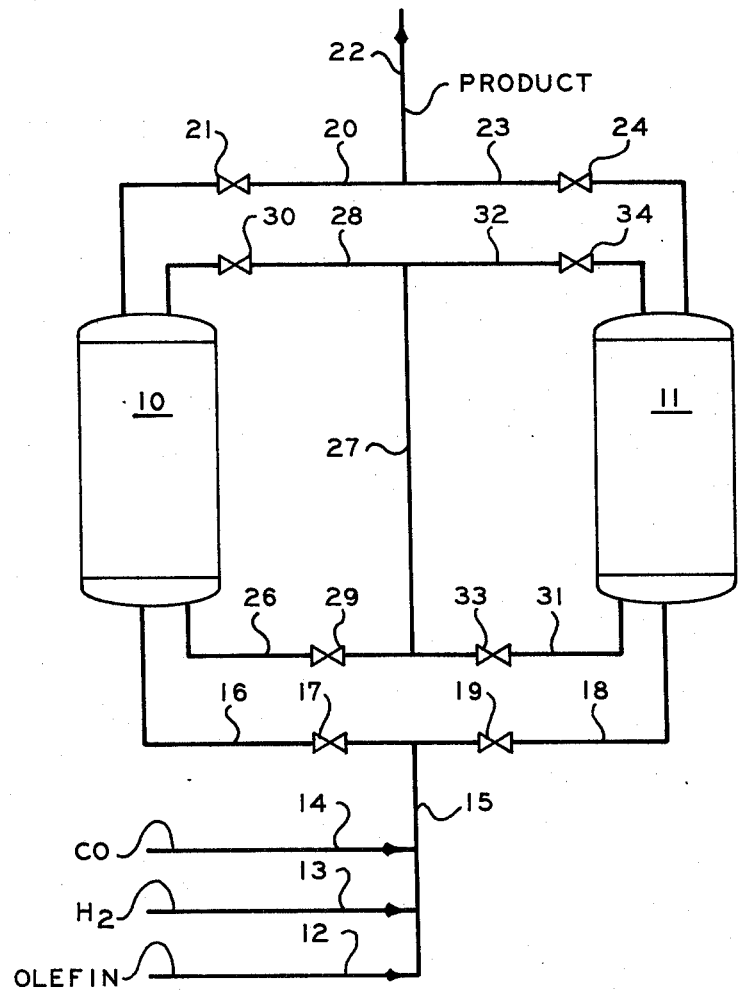

In the drawing, FIG. 1 is a schematic representation of apparatus which can be employed to carry out the hydroformylation process. FIG. 2 illustrates the infrared absorption characteristics of p-styryldiethylphosphine.

A catalyst system for the hydroformylation process is formed by contacting a solid trivalent phosphorus-containing polymer with a material which serves to promote the reaction of olefinic materials with carbon monoxide and hydrogen. The materials which can be so employed are cobalt, rhodium, ruthenium, platinum and/or palladium, which are in such a form as to constitute a metal carbonyl under the reaction conditions. In general, cobalt is the preferred metal, and advantageously can be in the form of cobalt hydrocarbonyl or dicobalt octacarbonyl.

The phosphorus-containing polymers employed in the catalyst system are polymers of olefinically unsaturated phosphines having the formula:

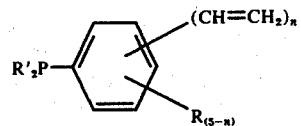

wherein each R is hydrogen or an alkyl group containing 1 to 4 carbon atoms, the total number of carbon atoms in all of the R substituents in each molecule not exceeding 12; each R' is a hydrocarbyl radical selected from the group consisting of alkyl, cycloalkyl, and aryl, and combinations thereof such as alkaryl, aralkyl, and the like, said hydrocarbyl radical containing 1 to 20 carbon atoms; and $n$ is 1 to 3. Examples of such olefinically unsaturated phosphines which can be used as monomers include o-styryldimethylphosphine, p-styryldiethylphosphine, m-styryldiisopropylphosphine, o-styryldihexylphosphine, m-styrylmethylphenylphosphine, p-styryldiphenylphosphine, o-styryldibenzylphosphine, m-styryldi-p-tolylphosphine, p-styryldicyclohexylphosphine, 2,4-divinylphenyldidecylphosphine, 2,3,5-trivinylphenylbis(3-methylcyclopentyl)phosphine, 2-methyl-4-vinylphenylbis(cycloheptylmethyl)phosphine, 2-ethyl-4-isopropyl-6-vinylphenylbis(2-ethylhexyl)phosphine, 2,4,6-tributyl-3,5-divinylphenyldieicosylphosphine, and the like, and mixtures thereof. When n in the above formula for the olefinically unsaturated phosphine is 2 or 3, the phosphine can be polymerized to a solid, crosslinked homopolymer, containing phosphorus in trivalent form, useful in the process of this invention. Particularly good results are obtained by use of a copolymer produced by polymerizing at least one of the olefinically unsaturated phosphines represented by the above formula with about 1 to 40 parts by weight, per 100 parts by weight of unsaturated phosphine, of a vinyl aromatic hydrocarbon. The vinyl aromatic hydrocarbon so employed can have any one of the following general formulas:

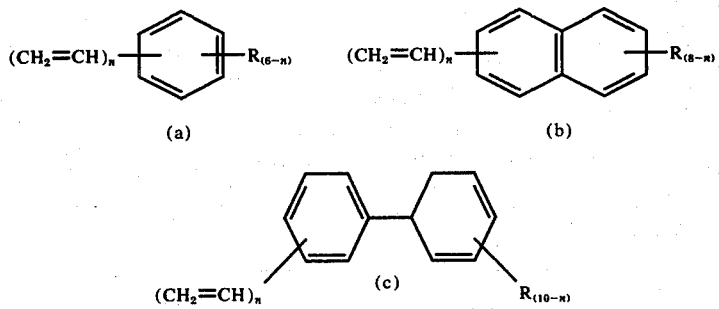

wherein each R and each n are as defined above. The substituents in the above Formulas (b) and (c) can be on either or both rings. Either the olefinically unsaturated phosphine or the vinyl aromatic hydrocarbon, or both, should have at least two vinyl groups to provide the desired crosslinked polymer. Examples of suitable vinyl aromatic hydrocarbons which can be employed include styrene, 1-vinylnaphthalene, 4-vinylbiphenyl, 4-methylstyrene, 2-ethylstyrene, 1,2-divinylbenzene, 1,3-divinylbenzene, 1,4-divinylbenzene, 1,2,4-trivinylbenzene, 1,3-divinylnaphthalene, 1,8-divinylnaphthalene, 1,3,5-trivinylnaphthalene, 2,4-divinylbiphenyl, 3,4′,5-trivinylbiphenyl, 1,2-divinyl-3,4-dimethylbenzene, 1,5,6-trivinyl-3,7-diethylnaphthalene, 1,3-divinyl-4,5,8-tributylnaphthalene, 2,2′-divinyl-4-ethyl-4′-propylbiphenyl, 2,4,4′-trivinyl-2′,3,3′-tributylbiphenyl, and the like, and mixtures thereof. The divinyl aromatic hydrocarbons are preferred, particularly the isomeric divinylbenzenes. Commerical divinylbenzene, which comprises a mixture of the isomeric ortho, meta, and para isomers, is quite suitable.

The preparation of the polymer can be carried out under a variety of reaction conditions. For example, reaction temperatures in the general range of 25° to 150° C. are suitable. Although reaction pressures up to 100 psig or higher can be used, pressures near atmospheric are usually preferred. Reaction times are generally in the range of 15 minutes to 150 hours. Although the polymerization can be carried out in the absence of a catalyst, ultraviolet light or catalysts such as 2,2′-azobis(2-methylpropionitrile) can be employed to promote the polymerization. Preferably, a solvent is used, e.g., an aromatic hydrocarbon such as benzene, toluene, or xylene or a saturated hydrocarbon such as hexane, octane, cyclohexane, or methylcyclopentane. It is desirable that the polymerization be carried out in an inert atmosphere such as nitrogen to prevent oxidation of the phosphine or polymer thereof.

The catalyst system can be formed by any convenient procedure. For example, cobalt naphthenate, dicobalt octacarbonyl, or other hydrocarbon-soluble compound or compounds of cobalt, rhodium, ruthenium, platinum, and/or palladium can be dissolved in an aromatic, paraffinic, or cycloparaffinic material or in the olefinic substance itself which is to be employed in the oxo reaction. The resulting solution can then be placed in contact with the polymer under an atmosphere of carbon monoxide and hydrogen at a temperature in the general range of 200°–450° F. The mixture can be agitated until equilibrium has been attained between the metal on the polymer and metal in solution. This usually requies from about 10 seconds to about 1 hour. However, the catalyst system can actually be formed in the reaction chamber itself. The amount of metal on the polymer support is of the order of 0.04 to 4, preferably 0.1 to 2, millimoles of metal per gram of polymer support.

The oxo reaction is carried out by contacting an olefinic substance with carbon monoxide and hydrogen in the presence of the catalyst system of this invention. The reaction is generally carried out at pressures, under operating conditions, in the range of 600 to 5000 psig of hydrogen and carbon monoxide, with about 1500–3500 psig being preferred. In general, alcohol production increases at higher pressures. The reaction temperature depends in part on the pressure employed and the reaction products desired. Temperatures generally are in the range of about 200 to 450° F., preferably 300°–400° F. The residence time is of the order of 1 minute to 10 hours, preferably 10 minutes to 6 hours. If desired, a solvent which is inert under the reaction conditions employed can be used.

The hydroformylation process is applicable to the reaction of any alphatic, either cyclic or acyclic, compound having at least one ethylenic carbon-to-carbon linkage, and is particularly applicable to olefinic hydrocarbons containing from 2 to about 12 carbon atoms. Both conjugated and nonconjugated olefins can be employed. Cyclic compounds, particularly hydrocarbons having 5 or 6 carbon atoms in a ring structure, can be reacted. The process is also applicable to the reaction of nonhydrocarbons containing ethylenic carbon-to-carbon linkages. In general, the catalyst system can be employed to advantage in carrying out the various hydroformylation reactions enumerated in U.S. Pat. No. 3,231,621.

In carrying out the hydroformylation process, at least 1 mole of carbon monoxide and 2 moles of hydrogen are required for each mole of olefinic substance when alcohols are to be produced. In the production of aldehydes, the hydrogen requirement is only half as great as in alcohol production. Although the mole ratio of hydrogen to carbon monoxide can be varied, depending in part on the products desired, this mole ratio generally will be at least 1. In some instances, the rate of reaction as well as the yield of desired products can be increased by increasing the mole ratio of hydrogen to carbon monoxide above 1.

The catalyst system is quite effective in carrying out oxo reactions with commercially available feed streams containing sulfur compounds, which are considered to be catalyst poisons in conventional oxo reactions. It is believed that the polymer portion of the catalyst system may act as a reservoir for the soluble metal, and release additional metal to replace that which may be tied up by the catalyst poisons.

As previously mentioned, the solid polymer employed in preparing the catalyst system can also be used to advantage to remove catalyst residues from the reaction products. A system for carrying out the process of this invention, including catalyst residue removal, is illustrated schematically in FIG. 1 of the accompanying drawing. The apparatus therein illustrated comprises two chambers 10 and 11 which can be any suitable vessels of configurations capable of retaining the solid polymer of the catalyst system of this invention. For example, these chambers can be provided with screens at the two ends to retain the catalyst. It will be assumed that reactor 10 initially contains the complete catalyst system, whereas reactor 11 initially contains only the solid polymer component of the catalyst system. Olefinic feed, hydrogen and carbon monoxide are introduced through respective conduits 12, 13 and 14 which communicate with a common inlet conduit 15. Conduits 12, 13 and 14 can be provided with flow control means, not shown, to regulate the rates of introduction of the feed materials. A conduit 16, having a valve 17 therein, communicates between conduit 15 and a first inlet of reactor 10. A corresponding conduit 18, having a valve 19 therein, communicates between conduit 15 and reactor 11. A conduit 20, having a valve 21 therein, communicates between an outlet of reactor 10 and a common outlet conduit 22. A similar conduit 23, having a valve 24 therein, communicates between reactor 11 and conduit 22. A second inlet of reactor 10 is connected to a second outlet thereof by conduits 26, 27 and 28. Valves 29 and 30 are disposed in respective conduits 26 and 28. Similarly, a second inlet of reactor 11 is connected to a second outlet thereof by conduits 31, 27 and 32. Valves 33 and 34 are disposed in respective conduits 31 and 32.

At the beginning of the reaction cycle, valves 17, 30, 33 and 24 are open and valves 19, 34, 29 and 21 are closed. Thus, the feed materials flow from conduit 15 through conduit 16, reactor 10, conduits 28, 27 and 31, reactor 11 and conduit 23 to outlet conduit 22. The oxo reaction takes place in reactor 10, and the effluent stream passes through reactor 11. The polymer contained within chamber 11 serves to remove catalyst residues from the reaction products. Any cobalt, or other metal catalyst, which may be entrained in the reactor effluent, is deposited on the solid polymer in reactor 11 and is thereby removed from the effluent stream. This operation continues until the polymer in reactor 11 is no longer capable of removing the desired quantity of catalyst residue and/or until the catalyst in reactor 10 has lost its desired activity because of the removal of metal with the reactor effluent stream. At this time, the system can be reversed so that chamber 11 serves as the reaction chamber and chamber 10 serves as the catalyst scavenging bed. This is accomplished by opening valves 19, 34, 29 and 21 and closing valves 17, 30, 33 and 24. In this procedure, the catalyst system is effectively formed in-situ in the vessel which serves to remove catalyst residues from the reaction products. The desired product or products can be separated from other materials in the reactor effluent by fractionation or any other convenient procedure.

In the procedure illustrated in the drawing, the vessel serving as the reactor is maintained in the temperature range of 200° to 450° F., preferably 300° to 400° F., with the pressure being in the range of 600 to 5000 psig, preferably 1500 to 3500 psig. The scavenging bed vessel is maintained in the temperature range of 50° to 250° F., with the pressure being in the range of 0 to 5000 psig. The residence time in the scavenging bed vessel is generally in the range of 10 seconds to 1 hour. Suitable heat exchangers and compressors, not shown, can be associated with the illustrated apparatus to maintain these conditions.

The catalyst residue removal system can also be used to treat effluent streams from conventional hydroformylation reactions employing any of the metals listed above as catalysts.

The p-styryldiethylphosphine of this invention can be produced by the procedure set forth hereinafter in Example II. In another embodiment of this invention, solid polymers of p-styryldiethylphosphine are produced, as can be accomplished by the procedure set forth in Example II.

EXAMPLE I

Solid, crosslinked, phosphorus-containing polymer was prepared through the use of p-styryldiphenylphosphine as a monomer.

To prepare the p-styryldiphenylphosphine, 0.1 mole of p-chlorostyrene was added to 0.1 gram-atom of magnesium in 50 ml. of refluxing tetrahydrofuran in a nitrogen atmosphere. After formation of the Grignard was complete, 0.1 mole of diphenylchlorophosphine was added dropwise to the mixture at 0° C. Hydrolysis of the reaction mixture with ammonium chloride solution, extraction with tetrahydrofuran, drying, and evaporation of the solvent left a yellow oil. Crystallization from hexane gave 14.5 grams of product melting at 71°–75° C. Combination of several preparations and crystallization from hexane gave p-styryldiphenylphosphine, used subsequently for polymerization, as a white crystalline solid melting at 76°–78° C. Analysis, Calcd. for $C_{20}H_{17}P$: C, 83.3%; H, 5.94%; P, 10.7%. Found: C, 82.8%; H, 6.0%; P, 10.87%.

The above monomer was used to prepare two batches of solid, crosslinked, phosphorus-containing polymer herein designated as Polymer A and Polymer B.

In the preparation of Polymer A, a mixture of 10 grams of p-styryldiphenylphosphine, 1 gram of a commercial mixture of 50 weight percent isomeric divinylbenzenes, 0.3 gram of 2,2'-azobis(2-methylpropionitrile), and 50 ml of benzene was refluxed for 10 hours in a nitrogen atmosphere. The polymer was precipitated by pouring the reaction mixture slowly into methanol. Washing the precipitate with hexane, pentane, and ether gave 11 grams of free-flowing white polymer, Polymer A, softening at about 200° C. and melting above 320° C. Analysis. Found: C, 83.1%; H, 6.4%; P, 9.2%.

In the preparation of Polymer B, a mixture of 17.6 grams of p-styryldiphenylphosphine, 3.5 grams of a commercial mixture of 50 weight percent isomeric divinylbenzenes. 0.4 gram of 2,2'-azobis(2-methylpropionitrile), and 50 ml. of benzene was refluxed in a nitrogen atmosphere for 2-½ hours, at the end of which time the polymer had gelled in the hot benzene. The benzene was removed and the residual solid was washed with hexane to give 21.1 grams of light yellow polymer, Polymer B. Analysis. Found: C, 84.1%; H, 6.9%; P, 8.8%.

Table I summarizes the results obtained in a series of runs in which Polymer A or Polymer B was employed in a 300-ml. autoclave used to convert 2-hexene to normal and branched $C_7$ aldehydes and normal and branched $C_7$ alcohols in an oxo reaction carried out at a batch process. In each run an equimolar mixture of carbon monoxide and hydrogen at a total pressure of 1500–3300 psig at operating temperature was used. The initial run was made using 3 grams of the above Polymer A, 50 ml. of cyclohexane, 25 ml of 2-hexene, and 3 ml. of a benzene solution of 0.42 gram of dicobalt octacarbonyl. In each of Runs 2 and 3, after decanting the products of the preceding run from the polymer, 50 ml. of cyclohexane and 25 ml of 2-hexene were added, and the autoclave each time was repressured with carbon monoxide and hydrogen. In each of Runs 4, 5, and 6, after decanting the products of the preceding run from the polymer, 75 ml of 2-hexene was added, and the autoclave each time was repressured with carbon monoxide and hydrogen. For Run 7 the polymer was replaced with another 3-gram portion of Polymer A, and 75 ml. of 2-hexene and 1 ml. of a benzene solution of 0.14 gram of dicobalt octacarbonyl were added prior to pressuring with carbon monoxide and hydrogen. In Run 8, after decanting the products of Run 7 from the polymer, 75 ml. of 2-hexene was added prior to repressuring with carbon monoxide and hydrogen. For Run 9 the polymer was replaced with 3 grams of Polymer B, and 75 ml. of 2-hexene and 1 ml. of a benzene solution of 0.14 gram of dicobalt octacarbonyl were added prior to pressuring with carbon monoxide and hydrogen. In each of Runs 10 and 11, after decanting the products of the preceding run from the polymer, 75 ml. of 2-hexene was added prior to repressuring with carbon monoxide and hydrogen. In each of the runs in Table I the conversion of 2-hexene was greater than 90 percent.

reaction carried out as a batch process. In each run an equimolar mixture of carbon monoxide and hydrogen

TABLE I

| Run | Temp., °F. | Time, hr. | Co in Effluent, ppm | Weight Ratio of Products | | | |
|---|---|---|---|---|---|---|---|
| | | | | Alcohol | | Aldehyde | |
| | | | | Normal | Branched | Normal | Branched |
| 1 | 250 | 1.5 | 570 | Trace | Trace | 67 | 33 |
| 2 | 350–400 | ~2 | 45 | 21 | 14 | 34 | 31 |
| 3 | 350 | 2 | 18 | 10 | 6 | 47 | 37 |
| 4 | 350 | 4 | 15 | 9 | 5 | 43 | 43 |
| 5 | 320–350 | 5 | 21 | 8 | 6 | 42 | 44 |
| 6 | 350–360 | 4.5 | 7 | 7 | 5 | 43 | 45 |
| 7 | 360 | 4 | —a | 4 | 3 | 50 | 43 |
| 8 | 380–400 | 6 | —a | 13 | 8 | 38 | 41 |
| 9 | 380–400 | 4 | —a | 33 | 23 | 24 | 20 |
| 10 | 370–380 | 4 | —a | 9 | 8 | 42 | 41 |
| 11 | 370–380 | 5 | —a | 14 | 9 | 37 | 40 | aNot determined.

The results of these runs demonstrate that cobalt-containing, solid, crosslinked polymers derived from p-styryldiphenylphosphine can be used repeatedly in an oxo reaction without further additon of cobalt catalyst. The ability of the polymer to bind the cobalt is also demonstrated.

EXAMPLE II p-Styryldiethylphosphine was prepared by adding 0.145 mole of diethylchlorophosphine to the Grignard reagent at 0° C. formed from 0.16 mole of p-chlorostyrene and 0.18 gram-atom of magnesium in 50 ml. of tetrahydrofuran in a nitrogen atmosphere. Hydrolysis with aqueous ammonium chloride, extraction with tetrahydrofuran, drying, and distillation gave 8.3 grams of p-styryldiethylphosphine boiling at 81°–83° C. at 0.1–0.15 mm Hg. Analysis. Calculated for $C_{12}H_{17}P$: C, 75.0%; H, 8.85%. Found: C, 73.7%; H, 9.2%. Gas chromatographic analysis indicated the purity of the product to be greater than 99 weight percent, and the infrared and nuclear magnetic resonance spectra were consistent with those to be expected for a compound of the assigned structure, as set forth in detail hereinafter in Example III.

To prepare a solid, crosslinked, phosphorus-containing polymer, 7.8 grams of p-styryldiethylphosphine, 3 grams of a commercial mixture of 50 weight percent isomeric divinylbenzenes, and 1.5 grams of 2,2'-azobis(2-methylpropionitrile) were heated in 50 ml. of benzene at reflux for 10 hours in a nitrogen atmosphere. Evaporation of the benzene, washing of the residue with hexane, and drying gave 10.7 grams of free-flowing, light yellow, solid, crosslinked polymer of p-styryldietylphosphine. Analysis. Found: C, 73.3%; H, 8.8%.

Table II summarizes the results obtained in a series of runs in which the above polymer of p-styryldiethylphosphine was employed in a 300-ml. autoclave used to prepare normal and branched $C_7$ aldehydes and normal and branched $C_7$ alcohols from 2-hexene in an oxo reaction carried out as a batch process. In each run an equimolar mixture of carbon monoxide and hydrogen at a total pressure of 1500–3300 psig at operating temperature was used. The initial run was made using 3 grams of the polymer, 50 ml. of cyclohexane, 25 ml of 2-hexene, and 1 ml. of a benzene solution of 0.22 gram of dicobalt octacarbonyl. In each of the succeeding runs, after decanting the products of the preceding run from the polymer, 75 ml. of 2-hexene was added, and the autoclave each time was repressured with carbon monoxide and hydrogen. In each of the runs the conversion of 2-hexene was greater than 90 percent.

TABLE II

| Run | Temp., °F. | Time, hr. | Co in Effluent, ppm | Weight Ratio of Products | | | |
|---|---|---|---|---|---|---|---|
| | | | | Alcohol | | Aldehyde | |
| | | | | Normal | Branched | Normal | Branched |
| 1 | 300–385 | 4.5 | 790 | 70 | 15 | 11 | 4 |
| 2 | 350–400 | 4 | 68 | 34 | 14 | 29 | 23 |
| 3 | 340–400 | 5 | 9 | 22 | 14 | 31 | 33 |
| 4 | 400 | 2.5 | 7 | 16 | 11 | 36 | 37 |
| 5 | 350–400 | 6 | 6 | 26 | 14 | 30 | 30 |

The results of these runs demonstrate that a cobalt-containing, solid, crosslinked polymer derived from p-styryldiethylphosphine can be used repeatedly in an oxo reaction without further addition of cobalt catalyst. Also demonstrated is the ability of the polymer to bind the cobalt.

EXAMPLE III

The material produced in Example II was identified as p-styryldiethylphosphine by infrared and nuclear magnetic resonance measurements.

The infrared spectrum obtained is illustrated in FIG. 2 of the drawing. Th observed absorption bands represent the following structure:

| Band (microns) | Structure |
|---|---|
| 3.4 – 3.5 | C—H stretch |
| 6.3 | C=C stretch (from vinyl group) |
| 6.7 – 7.3 | C—H bending modes |
| 10.1 and 11.0 | typical of $\underset{H}{\overset{R}{\diagdown}}C=C\underset{H}{\overset{H}{\diagup}}$ |
| 12.0 | characteristic of a p-disubstituted benzene |

The nuclear magnetic resonance (NMR) data show a structural formula as follows:

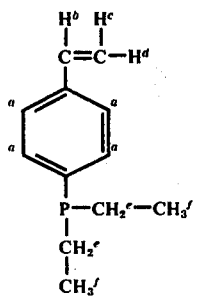

| | Chemical Shift Position | Multiplicity | Assignment | No. of Protons Experimentally Found |
|---|---|---|---|---|
| $H^a$ | 2.37–2.83 tau | disturbed singlet | aromatic ring protons | 4.0 |
| $H^b$ | 3.00–3.58 tau | quartet of singlets | nonterminal olefinic proton in a vinyl group | 0.9 |
| $H^c$ & $H^d$ | 4.03–4.97 tau | two quartets | two nonequivalent terminal olefinic protons in vinyl group | 1.9 |
| $H^e$ | 8.10–8.60 tau | two quartets | methylene alpha to —P | 4.1 |
| $H^f$ | 8.67–9.33 tau | two triplets | methyl beta to —P | 6.1 |

Conjugation within the styryl part of the molecule is thought to maintain the vinyl group and the benzene ring in the same plane. This produces a nonequivalence in the aromatic ring protons resulting in the disturbed appearance of the aromatic resonance, $H^a$.

The protons making up the vinyl group ($H^b$, $H^c$, $H^d$) give a characteristic ABC resonance whose fine structure is determined by 3 different chemical shifts ($\nu$) and 3 coupling constants (J).

| | |
|---|---|
| $\nu H^b = 3.3$ tau | $J_{b,c} = 10.5$ cps |
| $\nu H^c = 4.8$ tau | $J_{b,d} = 17.5$ cps |
| $\nu H^d = 4.3$ tau | $J_{c,d} = 1.5$ cps |

It can be observed that the coupling constant between the trans protons, ($J_{b,d}$) is considerably larger than between the cis protons ($J_{b,c}$).

For the terminal olefinic protons, the lower field signal (4.3 tau) corresponds to the shorter distance from terminal olefinic proton to the benzene ring and is assigned to $H^d$ whereas the higher field signal (4.8 tau) is a longer distance from the ring and is assigned to $H^c$.

The hydrogen nuclei of the vinyl group in the styryl part of the molecule are observed to give anomalous chemical shifts. This is due largely to the effects of diamagnetic circulations of electrons in the aromatic ring (ring currents). Banwell and Sheppard, Molec. Phy., 3, 351 (1960), have estimated the necessary corrections to the vinyl chemical shifts for these ring currents. By applying these corrections the resulting chemical shifts were found to be correct for the styryl group.

The chemical shifts of the alkyl groups ($H^e$ and $H^f$) are downfield from their normal positions due to the electronegativity of the phosphorus atom. This part of the spectrum may be considered as a typical $A_3B_2$ system. The $J_{CH}$ -P coupling constant is <1 cps, which shows that for the alkyl methylenes two quartets are superimposed. The $J_{CH}$ -P coupling is known (Emsley et al., High Resolution NMR Spectroscopy, 1, 1966, Pergamon Press, p. 372) to be large and in this sample is found to be about 15 cps, so that 2 overlapping triplets for the methyl group resonances are obtained.

While this invention has been described in conjunction with presently preferred embodiments, it obviously is not limited thereto.

What is claimed is:
1. p-Styryldiethylphosphine.

* * * * *